(12) United States Patent
Farris

(10) Patent No.: US 7,232,446 B1
(45) Date of Patent: Jun. 19, 2007

(54) PNEUMATIC SUTURE INSTRUMENT

(76) Inventor: Alex F. Farris, 2134 Wooledge Dr., Birmingham, AL (US) 35226

( * ) Notice: Subject to any disclaimer, the term of this patent is extended or adjusted under 35 U.S.C. 154(b) by 649 days.

(21) Appl. No.: 10/345,517

(22) Filed: Jan. 16, 2003

(51) Int. Cl.
*A61B 17/04* (2006.01)

(52) U.S. Cl. ............ 606/144; 606/148; 606/146; 112/169

(58) Field of Classification Search .......... 606/146
See application file for complete search history.

(56) References Cited

U.S. PATENT DOCUMENTS

| | | | | |
|---|---|---|---|---|
| 2,611,366 A | * | 9/1952 | Mull | 606/146 |
| 4,224,947 A | * | 9/1980 | Fukuda | 606/146 |
| 4,557,265 A | * | 12/1985 | Andersson | 606/144 |
| 4,890,615 A | | 1/1990 | Caspari et al. | |

* cited by examiner

*Primary Examiner*—Anhtuan T. Nguyen
*Assistant Examiner*—Darwin P Erezo
(74) *Attorney, Agent, or Firm*—Smith, Gambrell & Russell

(57) ABSTRACT

The surgical suturing instrument incorporates a pressurized fluid suture feed system for passing a suture through the instrument and the tissues to be joined thereby. A fluid jet in communication with a suture feed conduit selectively entrains a suture in a stream of pressurized fluid, which carries the suture through the instrument's hollow tissue penetrating needle. The tissue penetrating needle may be shaped to direct the suture's free end to a point external the body cavity. Alternatively, a suture return conduit may be provided to engage the hollow tissue penetrating needle to receive and carry the suture's leading end to a point external the body cavity. External or internal pressurized fluid sources are utilized. A surface irregularity proximal the suture's leading end enhances the entrainment of the suture with the fluid stream. Individual, cartridge and spool fed sutures may all be utilized.

15 Claims, 14 Drawing Sheets

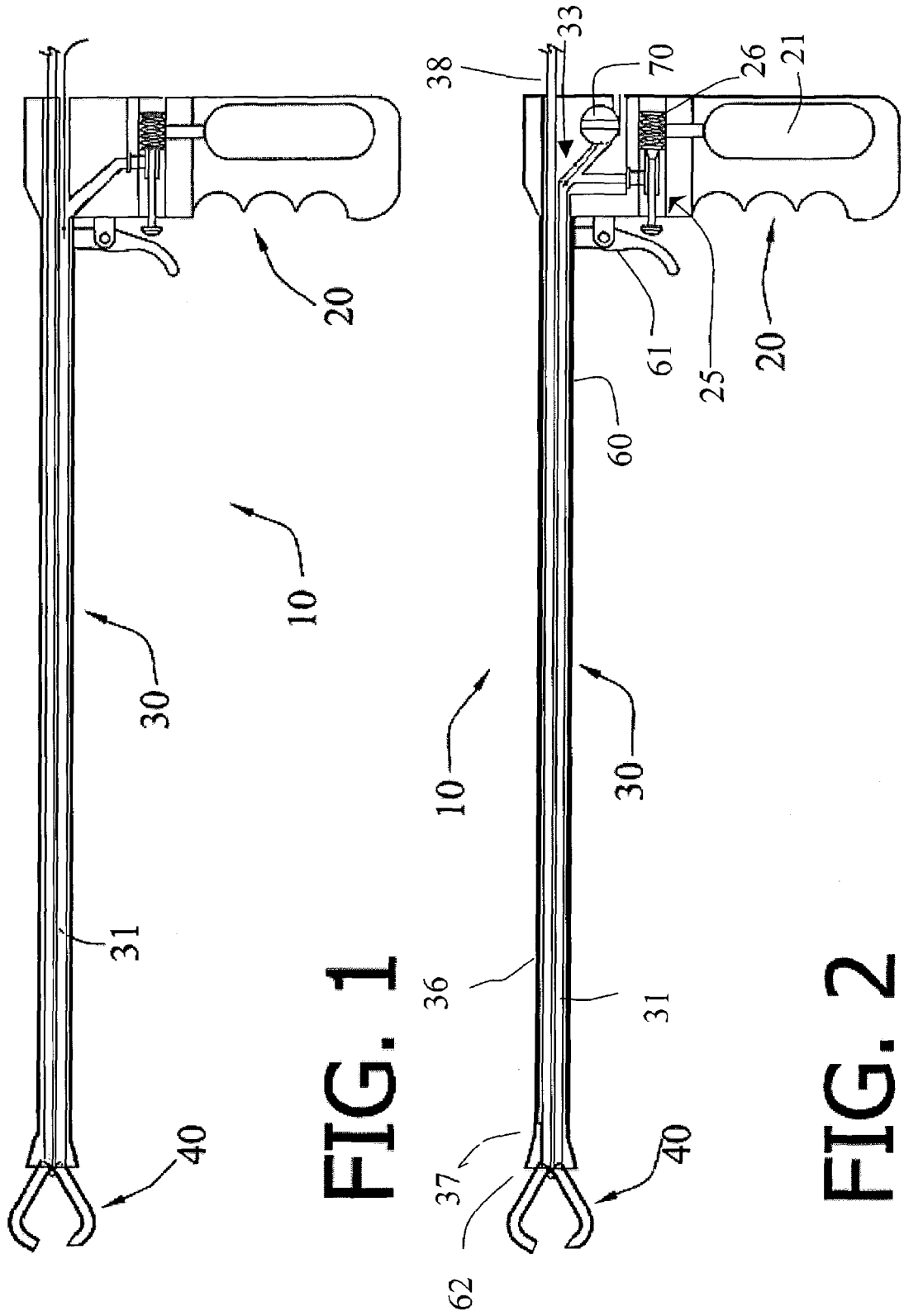

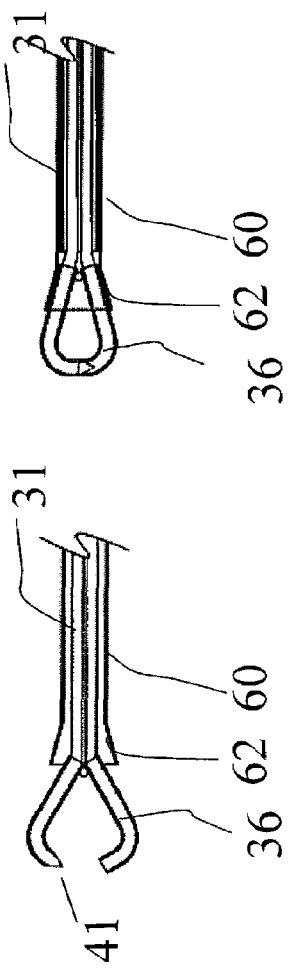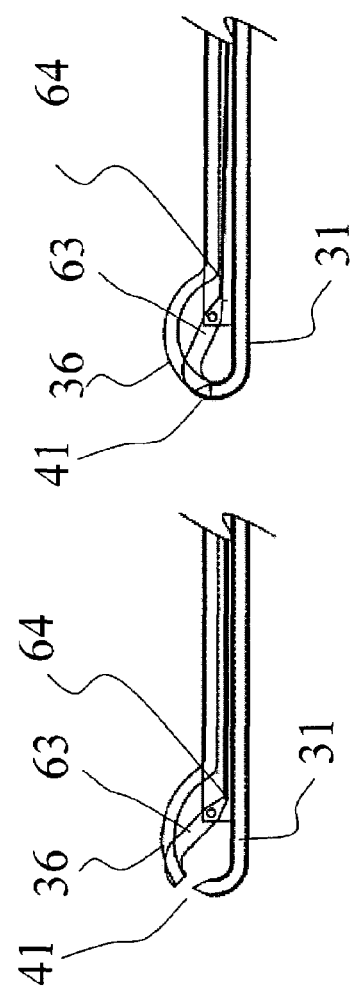

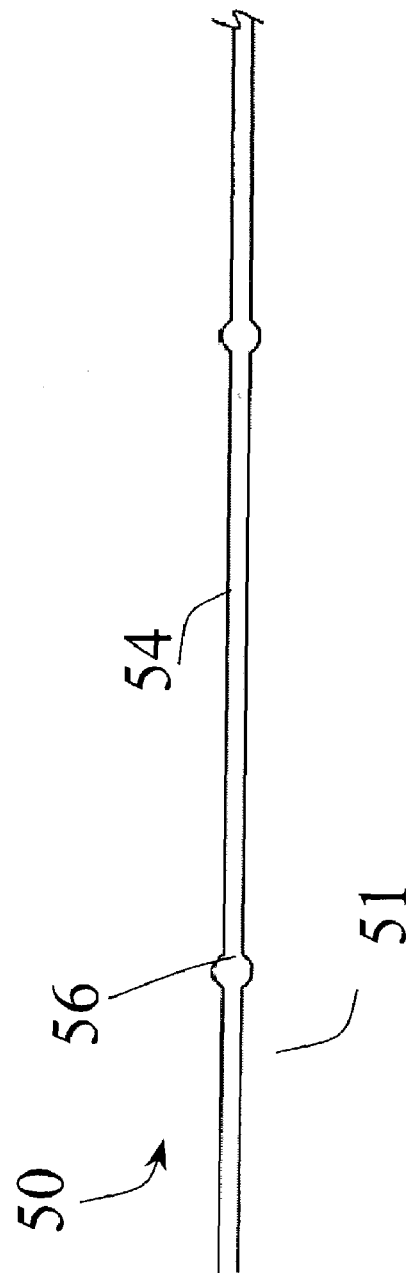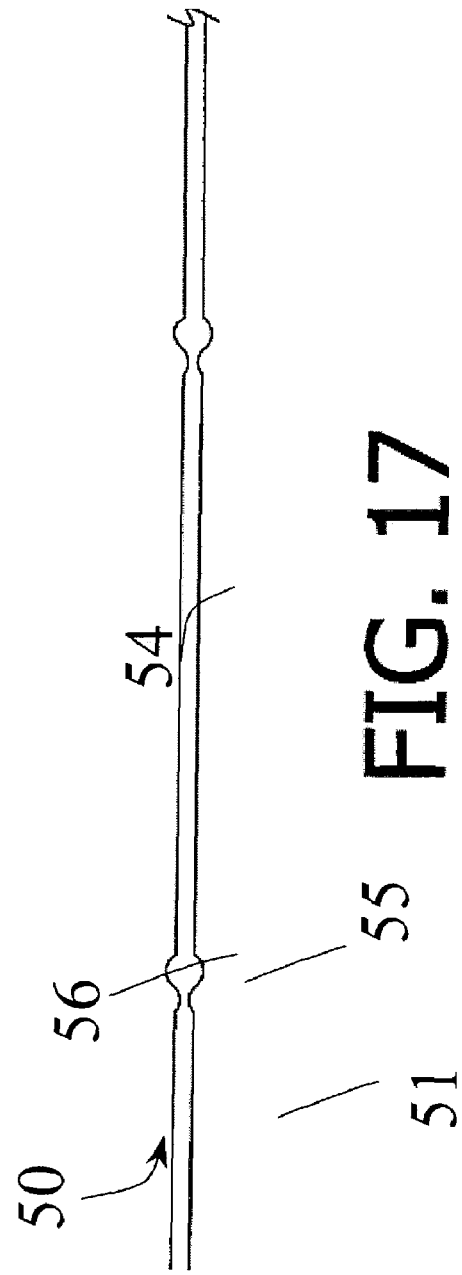

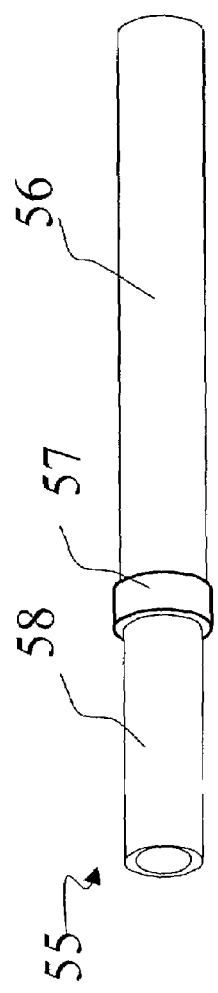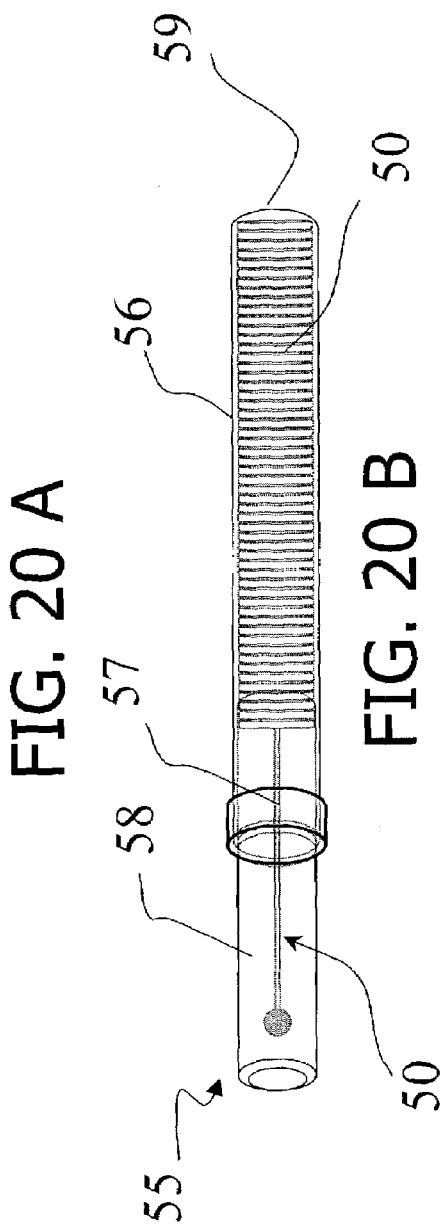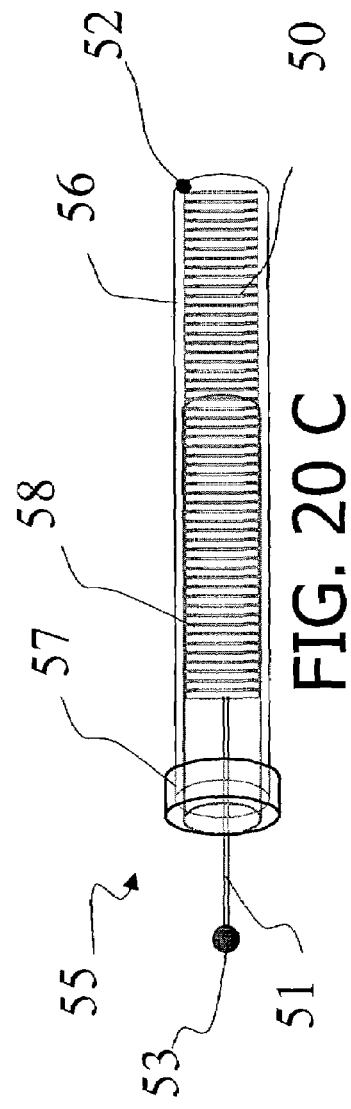

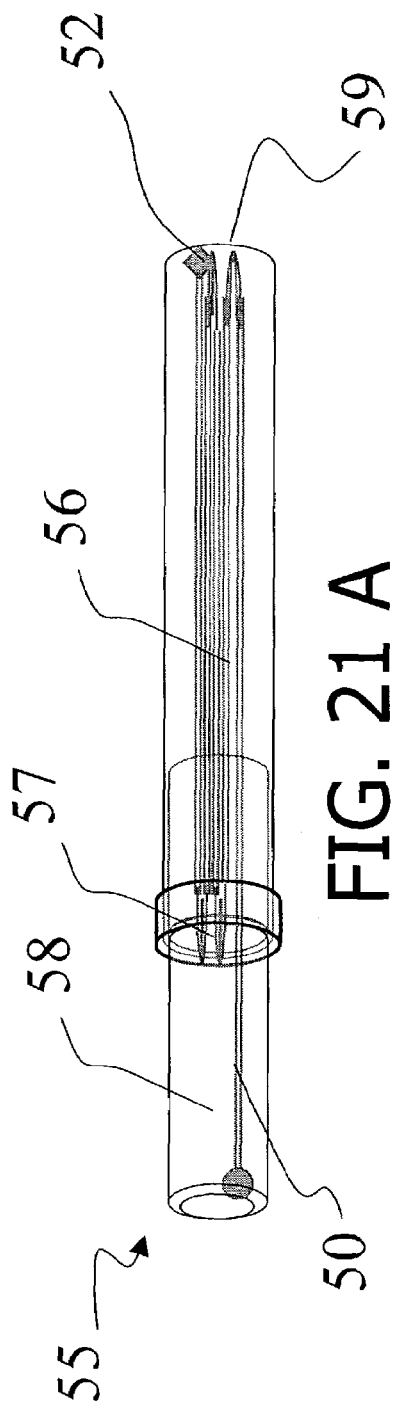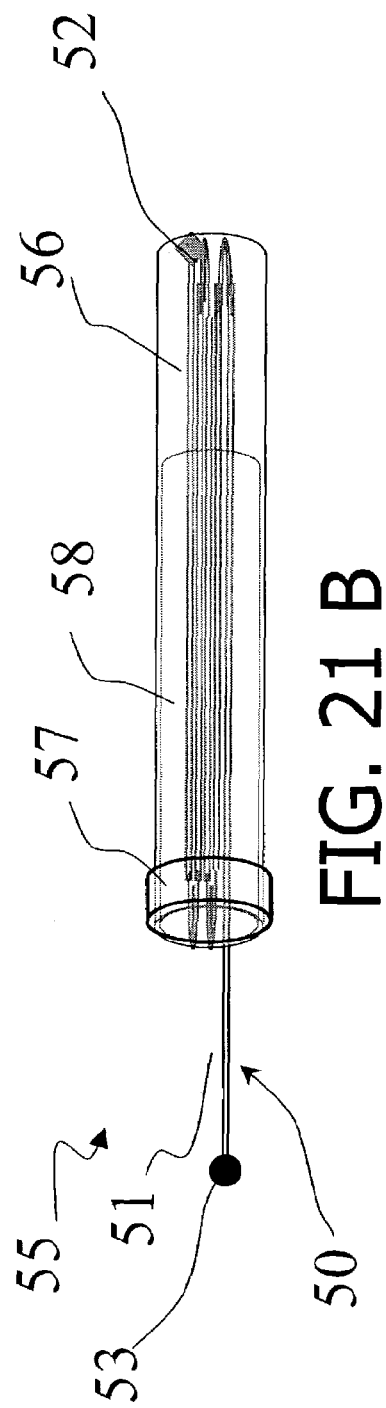

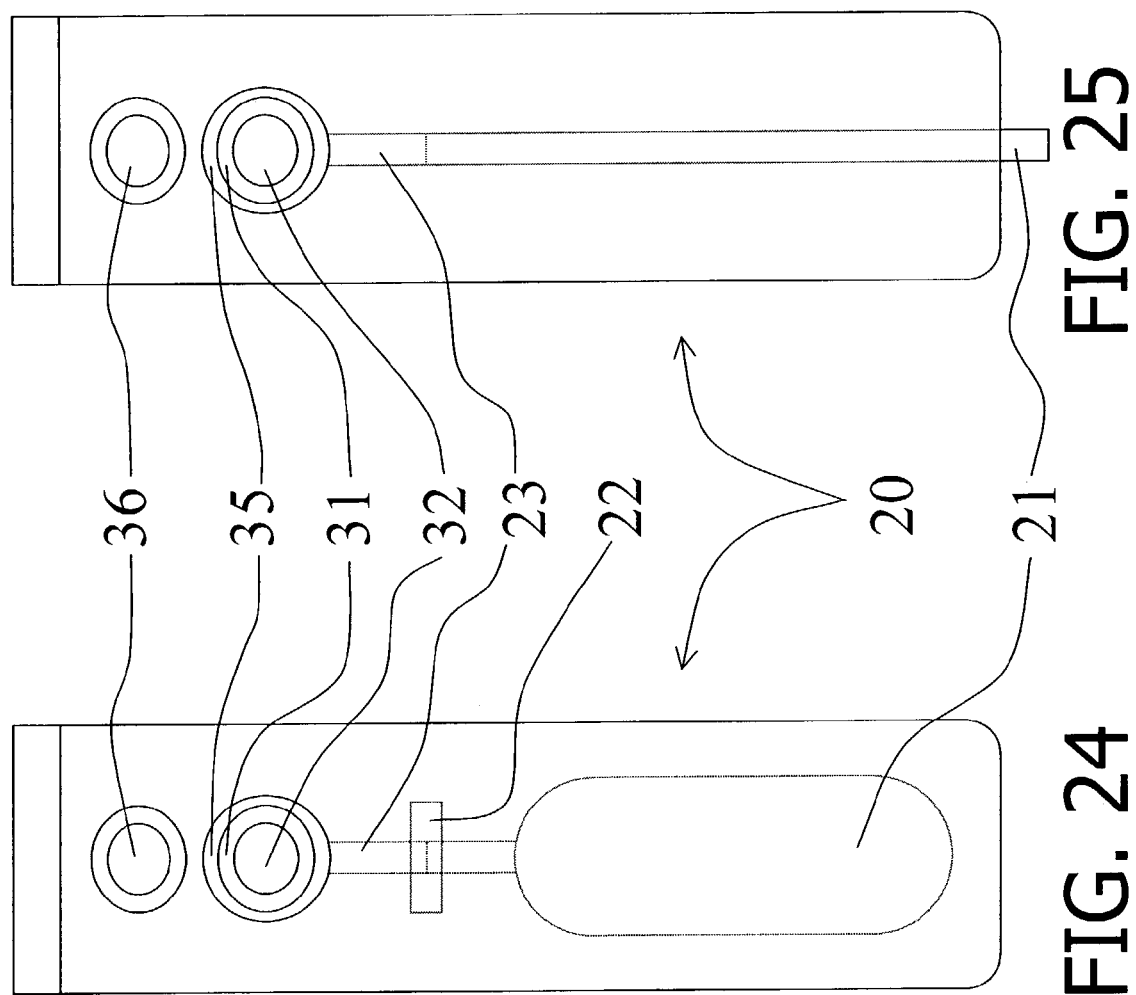

PNEUMATIC SUTURE INSTRUMENT

TECHNICAL FIELD

This invention relates to the field of suturing instruments used for stitching internal tissues of the body, such as in arthroscopic or endoscopic surgery. More particularly, the invention relates to a suturing instrument wherein the suture is fed through the instrument and the tissues to be joined by entrainment with a pressurized fluid. The preferred suture contemplated by the invention will have a surface irregularity to provide an enhanced frictional interface to facilitate entrainment in the fluid stream.

BACKGROUND OF THE INVENTION

In the field of arthroscopic surgery various suturing instruments have been used for stitching internal tissues of the body. An object of such surgical procedures is to minimize the invasiveness of the surgical instrument in performing a given surgical procedure, whether diagnostic or restorative. This object is achieved by making a small incision in the overlying tissue layers to provide the surgeon access the site of interest. The surgeon may then insert the surgical instrument through the small incision and perform the desired procedure.

In many procedures, the surgeon will need to insert a stitch to join body tissues at the site of interest. A suturing instrument such as that disclosed by Caspari, et al., in U.S. Pat. No. 4,957,498, will typically be used for joining tissues internal a patient's body. Such suturing instruments provide a hollow tissue penetrating needle through which the surgeon feeds a length of suture material. The suture material is fed by manipulation of a thumbwheel. After insertion of the suture material through the tissues the free end of the suture material is withdrawn with the instrument through the incision to a point external the patient's body. The surgeon then knots the suture material and manipulates the suture material to urge the knot back through the incision to a point adjacent to the joined tissues.

In practicing the invention disclosed by Caspari, the inventor has noticed the difficulty experienced by surgeons in manipulating the suture feed mechanism while maintaining the jaws of the instrument in the closed, tissue penetrating position. Moreover, the instrument disclosed by Caspari et al, requires the surgeon to coax the free end of the suture material to a point external the patient's body while at the same time feeding additional suture material by manipulation of the thumb wheel.

Should the surgeon loose the free end of the suture material during retraction of the instrument, additional intrusion into the body cavity is necessary to retrieve the suture free end for tying the desired stitch. In addition, should the free end of the suture be inadvertently pulled free of the tissue penetration points, additional tissue insult may be necessary to reinsert the suture material through the tissues. Accordingly, there is a need for a suturing instrument that provides an improved suture material feed and retraction mechanism.

BRIEF SUMMARY OF THE INVENTION

It is an object of the invention contemplated herein to provide an improved suture material feed mechanism for a surgical suturing instrument. According to the present invention, a pressurized fluid source is utilized to entrain and selectively feed a suture through the instrument and the tissues to be joined thereby. The suturing instrument comprises a handle portion, an elongated tubular member extending from the handle portion and a hollow tissue penetrating needle attached to the elongate tubular member distal the handle portion. A suture feed conduit extends in fluid communication between the hollow tissue penetrating needle and a suture feed inlet proximal the handle portion. A fluid jet, proximal the handle portion selectively communicates a pressurized fluid through the suture feed conduit and tissue penetrating needle. The suture feed inlet receives a leading end of the suture such that it is positioned relative the fluid inlet jet for selective entrainment of the suture with the pressurized fluid.

A preferred suture according to the present invention includes a surface irregularity, which defines a friction enhancing interface between the suture and the pressurized fluid. The surface irregularity is provided proximal a leading end of the suture and enhances the entrainment of the suture in the pressurized fluid stream. According to the present invention, the suture may be supplied to the instrument as an individual strand or as a plurality of sutures in a continuous strand. Each type of suture may be supplied on a spool or cartridge received by the instrument.

Individual suture strands are provided at a predetermined length corresponding to a required penetration depth to stitch the site of interest and should also allow the free ends of the strand to remain external the body for the surgeon to easily tie and manipulate the knot to a point adjacent the tissues to be joined.

A continuous strand of suture material has a plurality of surface irregularities spaced apart along its length. Each surface irregularity is spaced at a predetermined distance corresponding to a required penetration depth to stitch the site of interest and also allow the free ends of the strand to remain external the body for the surgeon to tie and manipulate the knot. A notch in the suture material adjacent a subsequent abrasion or protrusion is provided to facilitate separation of a delivered strand of suture material from the remaining strand of suture material.

Since it is a further object of the invention to improve the extraction of the suture free end to a point external the body, the suturing instrument of the present invention provides for a suture material return path between the site of interest and the instrument entry incision. This is achieved by reversing the direction of the fed suture and directing it on a suture return path to a point external the patient's body via the instrument entry incision.

In situations where a cannula is used to retract tissues overlying the site of interest open, the cannula opening may be used as the return path. In this instance, a hook shaped needle redirects the fed suture material outward the body. In situations where a cannula is not used, or where other organs or tissues may overly the site of interest, a return conduit is provided on the instrument to receive the leading end of the suture and carry it outwardly of the instrument entry incision. Positive reception of the suture material in the return conduit is provided by having the suture return conduit selectively engage with the tip of the tissue penetrating needle. Engagement of the return conduit with the tissue penetrating needle is provided by a lever or scissors assembly operable from the handle of the instrument.

Additional objects and advantages of the invention will be realized by reference to the accompanying drawings and the detailed description of the drawings.

BRIEF DESCRIPTION OF THE DRAWINGS

Various embodiments of my invention are depicted in the appended drawings which form a part of this disclosure and wherein:

FIG. 1 is a side sectional view of a suture instrument with a tissue penetrating needle in an open position;

FIG. 2 is a side sectional view of a suture instrument with a tissue penetrating needle in an open an a spooled suture feed;

FIG. 5 is a detail view of a sleeve actuated tissue penetrating needle closure with the needle in an open position;

FIG. 6 is a detail view of a sleeve actuated tissue penetrating needle closure with the needle in an open position;

FIG. 7 is a detail view of a lever actuated tissue penetrating needle closure with the needle in an open position;

FIG. 8 is a detail view of a lever actuated tissue penetrating needle closure with the needle in an open position;

FIG. 16 is a side view of a protruding suture surface irregularity; and

FIG. 17 is a side view of a compound suture surface irregularity.

FIG. 19 B is a perspective view of a suture spool;

FIG. 20 A is a perspective view of a suture cartridge;

FIG. 20 B is a partial sectional view of a suture cartridge with a wound suture material in its pre-insertion condition;

FIG. 20 C. is a partial sectional view of a suture cartridge with a wound suture material in its inserted condition;

FIG. 21 A is a partial sectional view of a suture cartridge with a folded suture material in its pre-insertion condition;

FIG. 21 B. is a partial sectional view of a suture cartridge with a folded suture material in its inserted condition;

FIG. 24 is an end view of a suture instrument handle with an internal pressurized fluid source; and FIG. 25 is an end view of a suture instrument handle configured for an external pressurized fluid source.

DETAILED DESCRIPTION OF THE INVENTION

Figure 18:
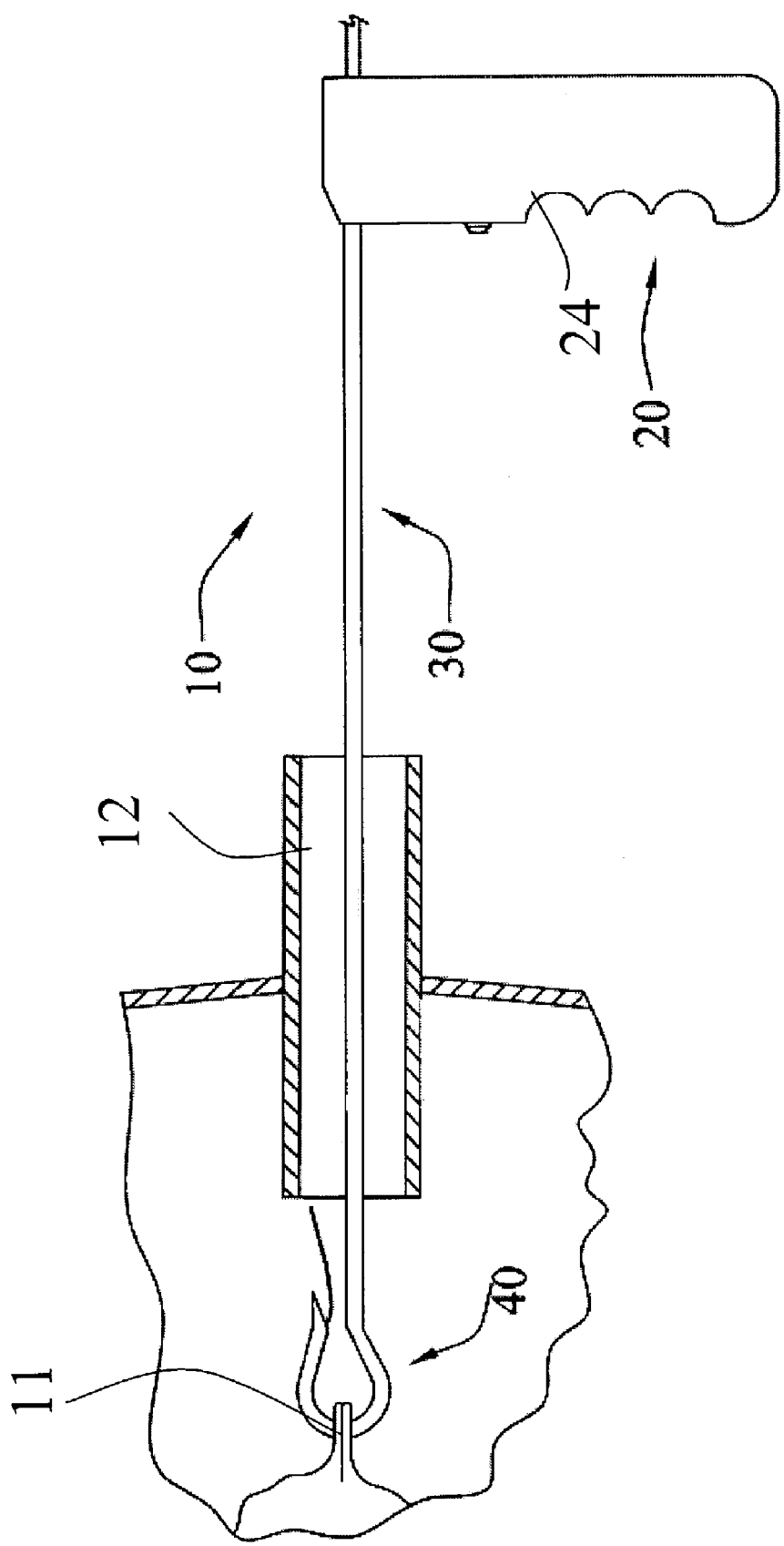
FIG. 18 is a partial side view of depicting a typical surgical procedure utilizing a hooked embodiment of the claimed suture instrument.

In reference to the drawings, the suture instrument 10 of the present invention comprises a handle portion 20, an elongated tubular member 30 extending from handle portion 20 and a hollow tissue penetrating needle 40 located at an end of elongated tubular member 30 distal handle portion 20. The length of elongated tubular member 30 is selected to correspond with a desired penetration depth within a body to reach the tissues to be joined 11 by a suture 50. The tissues to be joined 11 will also be referred to herein as site of interest. As is well known in the art, a cannula 12, such as that depicted in FIG. 18, is often used to retract the tissues at the entry incision 13 and improves access to the site of interest 11 by retracting the tissues overlying the site of interest 11. Cannula 12 will also perform a protective role for the overlying tissues by preventing undesirable instrument contact with the same. Accordingly, the length of elongated tubular member 30 must also account for any extension of canula 12 external the patient's body.

Handle portion 20 is adapted to be received in the hand of a surgeon to facilitate manipulation of the tissues at the site of interest and their suturing with instrument 10. Handle portion 20 is depicted in the drawings substantially perpendicular to elongated tubular member 30. However, this depiction is merely exemplary, as it is contemplated that more ergonomically advantageous handle configurations may be utilized for a particular surgical procedure or surgeon preference without departing from the scope of the present invention.

In practice, the surgeon manipulates the instrument to position hollow tissue penetrating needle 40 at a desired penetration point and urges the needle tip 41 through the first tissue to be joined. The surgeon then manipulates the instrument to a desired penetration point on a second tissue to be joined and urges needle tip 41 through the second tissue. Depending on the needle tip configuration, examples of which are provided in FIGS. 5–12, the surgeon will manipulate a trigger 27, such as that shown in FIGS. 1–4, or a conventional scissors assembly (not shown). Suture 50 may then be passed through the instrument and the tissues to be joined.

In the prior art, the surgeon was required to continuously manipulate the instrument during delivery of suture 50 through the instrument. Similarly, the surgeon must manipulate the instrument to continue to deliver suture 50 while coaxing free end 51 to a point external the patient's body. The pressurized fluid suture delivery taught by the present invention eliminates the need to manipulate the instrument during suture 50 delivery through the tissues and subsequent passage of leading end 51 to a point external the patient's body.

In the present invention, a suture feed conduit 31 extends between handle portion 20 and tissue penetrating needle 40. A suture feed inlet 32 is provided at a first end of suture feed conduit 31 proximal handle portion 20. Suture feed inlet 32, suture feed conduit 31 and hollow tissue penetrating needle 40 define a suture delivery path. A fluid jet 33, in communication with suture feed conduit 31, selectively communicates a pressurized fluid through suture feed conduit 31 and hollow tissue penetrating needle 40. Suture 50 is positioned to be entrained in the pressurized fluid stream for delivery through the tissues to be joined.

Fluid jet 33 is conveniently positioned in handle 20 and comprises a fluid jet inlet 23 and a fluid jet outlet 28, with fluid jet inlet 23 receiving a pressurized fluid source 21, provided by a cylinder 21 received in handle 20, as shown in FIG. 24, or from a source external the instrument 10, such as a pump or a pressurized fluid outlet common in an operating room environment and operatively connected to suture instrument 10, as shown in FIG. 25.

Fluid jet outlet 28 is positioned at an angle relative suture feed conduit 31 such that, upon release of the pressurized fluid source, a vacuum is induced at said suture feed inlet 23. Once suture 50 leading end 51 is positioned relative fluid jet 33 depression of activation button 24, permits the pressurized fluid to be delivered through fluid jet 33 and suture 50 is entrained with the pressurized fluid and passed through the instrument and the tissues to be joined. Delivery of leading end 51 to a point external a patient's body is provided by directing leading end 51 through a suture return path.

Figure 14:
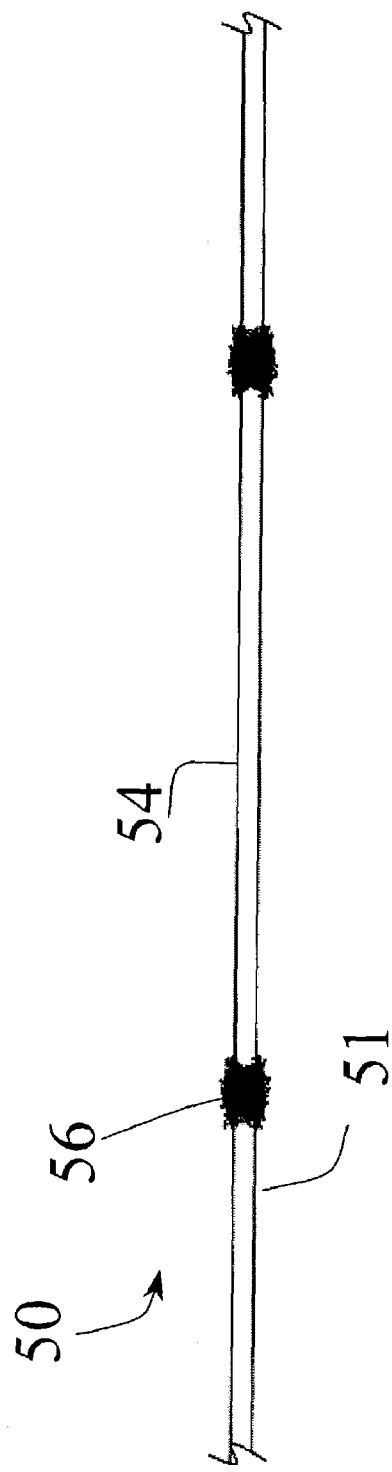
FIG. 14 is a side view of an abraided suture surface irregularity.
Figure 15:
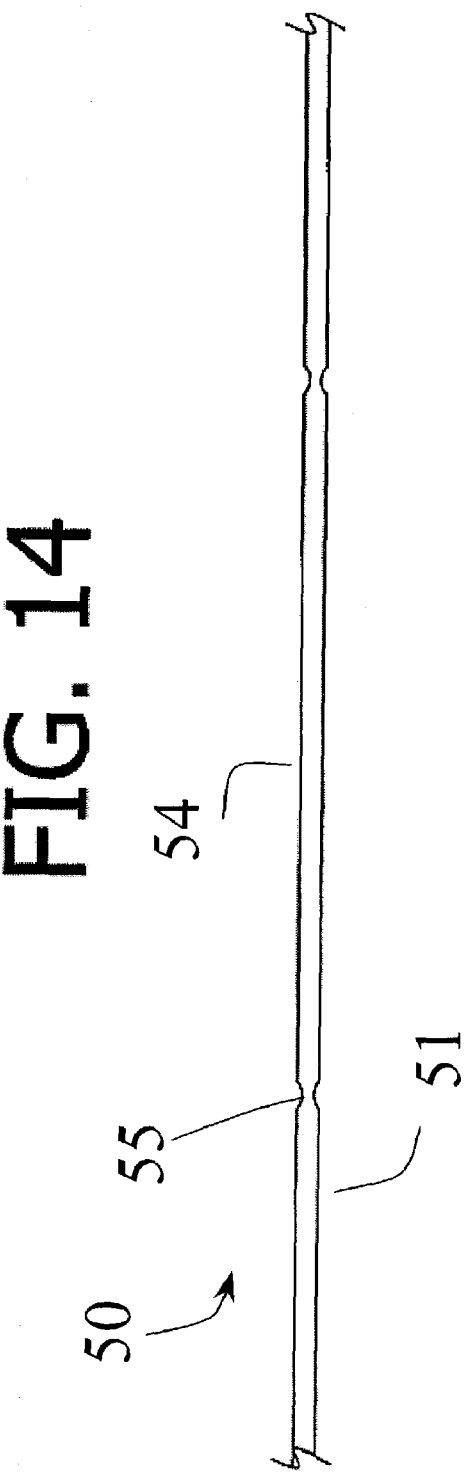
FIG. 15 is a side view of a constriction suture surface irregularity.

Referring to FIGS. 14–17, a preferred suture 50 will have a surface irregularity 53 positioned proximal leading end 51. Surface irregularity 53 is shaped to define a friction enhancing interface between the suture surface 54 and the pressurized fluid, facilitating entrainment of suture 50 with the pressurized fluid. As shown in FIG. 14, surface irregularity 53 is an abrasion or tuft on suture surface 54. As shown in FIG. 15, surface irregularity 53 comprises a constriction 55 in the cross sectional surface area of suture 50. Surface irregularity 53 may also be defined by a protrusion or bend 56 of suture material raised from the surface of the suture 50, as shown in FIG. 16. Similarly, the constriction 55 of FIG. 15 and the protrusion 56 of FIG. 16 may be combined to define the compound surface irregularity 53 depicted in FIG. 17. Each embodiment is suitable for use on individual suture strands, i.e. each strand will produce an individual stitch.

For continuous strands of suture material from which the surgeon may cut individual suture strands after retraction of instrument 10, a plurality of surface irregularities 53 are provided spaced apart along the length of suture 50. Each irregularity 53 is separated by a distance corresponding to a particular site of interest 11. The separation distance will depend upon the size of the patient and the depth of the site of interest 11 and also will allow the leading end 51 and trailing end 52 to be accessible to the surgeon at a point external the patient's body.

For continuous suture strands, the embodiments including a constriction 55 are particularly desirable. If a sufficient reduction in the cross sectional surface area is provided, constriction 55 will define a suture separator point, permitting the surgeon to readily sever an individual suture strand by pulling and snapping the trailing end 52 of the delivered preceding strand from the remaining length of suture material.

Figure 22:
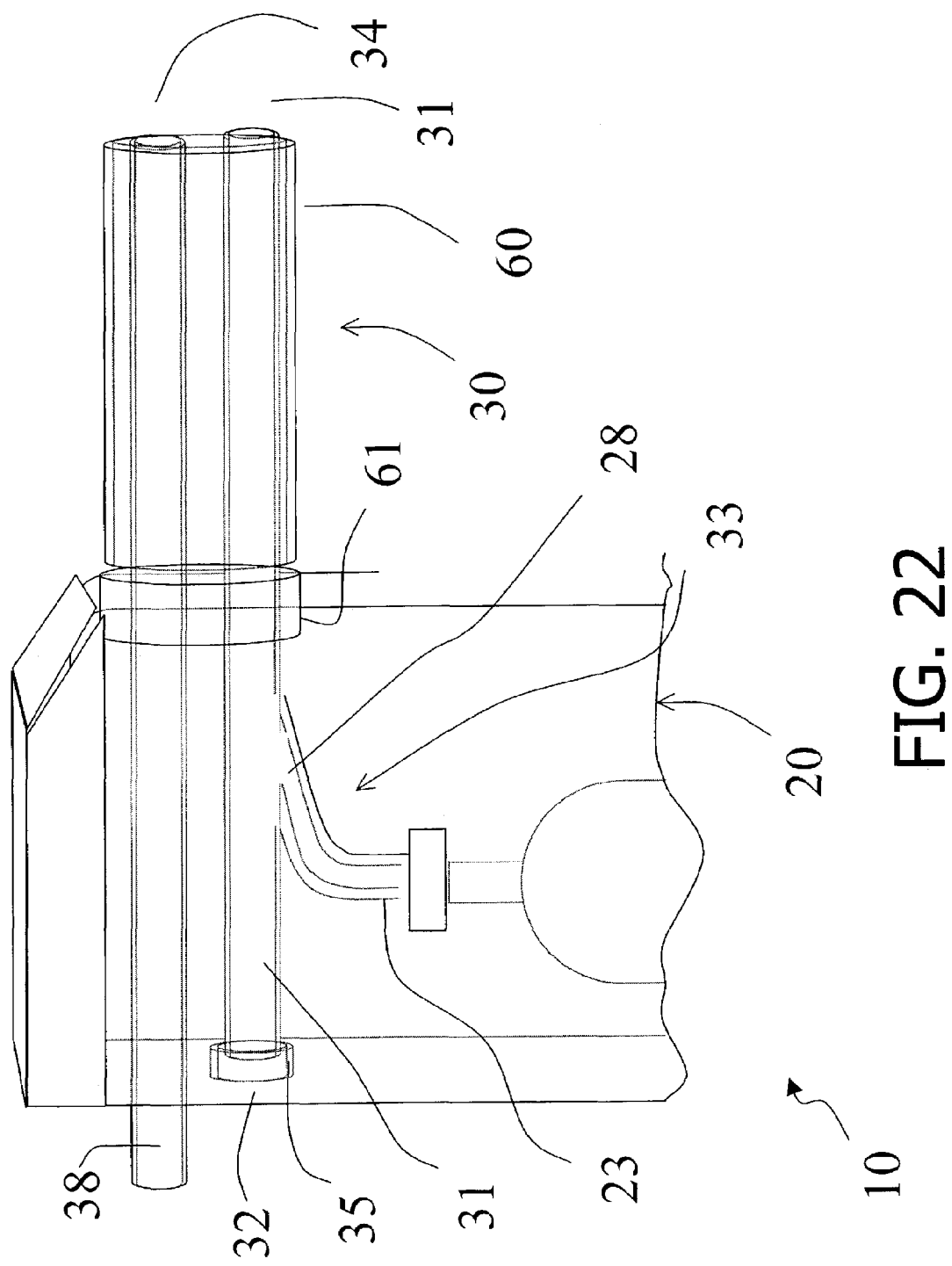
FIG. 22 is a partial perspective view of a cartridge receiving suture instrument.
Figure 23:
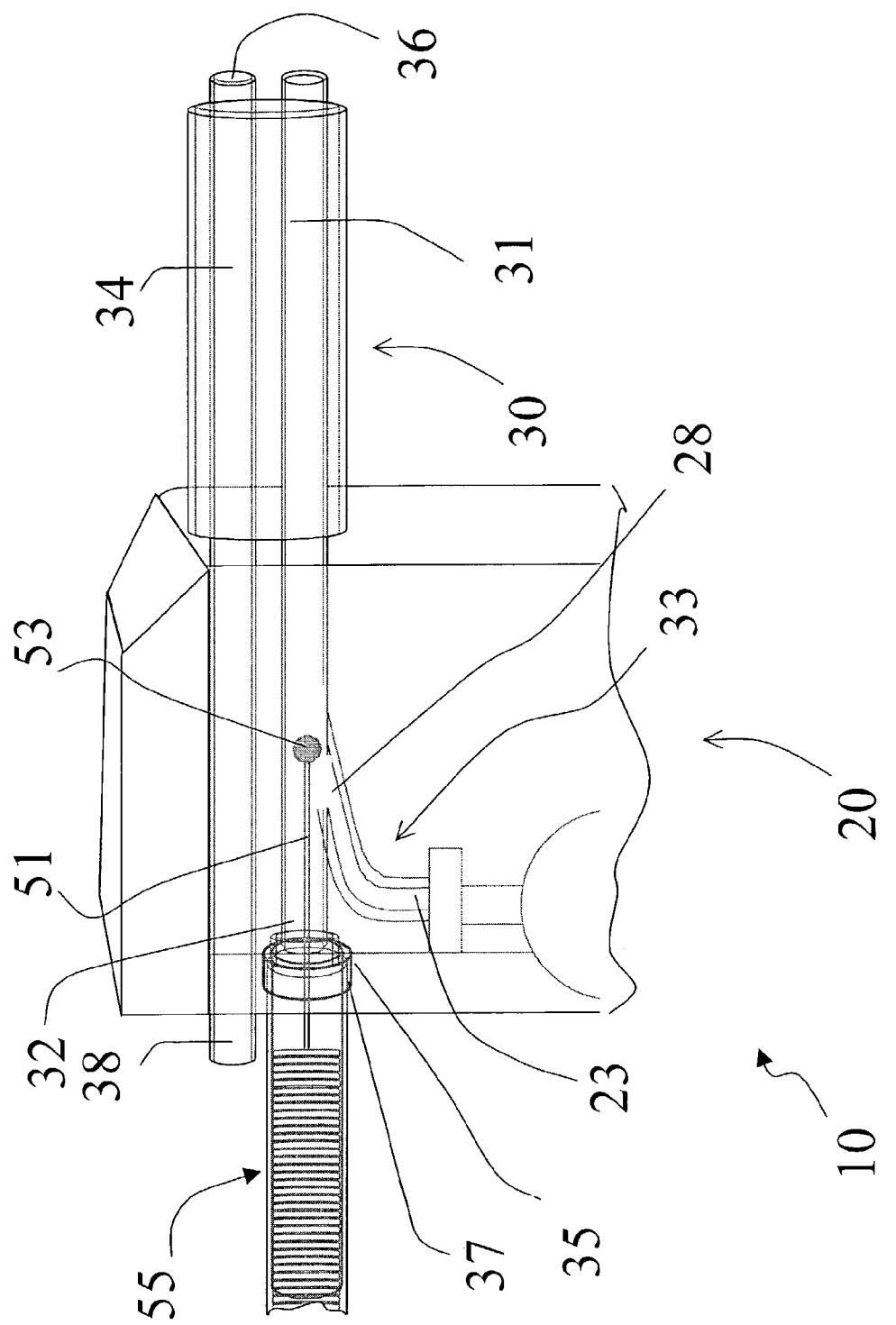
FIG. 23 is a partial perspective view of a cartridge receiving suture instrument with a cartridge inserted.

In addition to manually inserting a single suture strand 50, various methods are available for providing a suture 50 for use with suture instrument 10. As shown in FIG. 2, a spool 70, containing a strand of wound suture material 50 may be received in handle 20 such that leading end 51 may be positioned proximal fluid jet 33 for entrainment in the pressurized fluid stream. Alternately, as shown in FIGS. 21–23, suture 50 may be received in a cartridge 55 by winding, folding, or otherwise. Cartridge 55 may then be inserted into handle 20 such that suture leading end 51 is positioned proximal fluid jet 33 for entrainment in the pressurized fluid stream.

Figure 19:
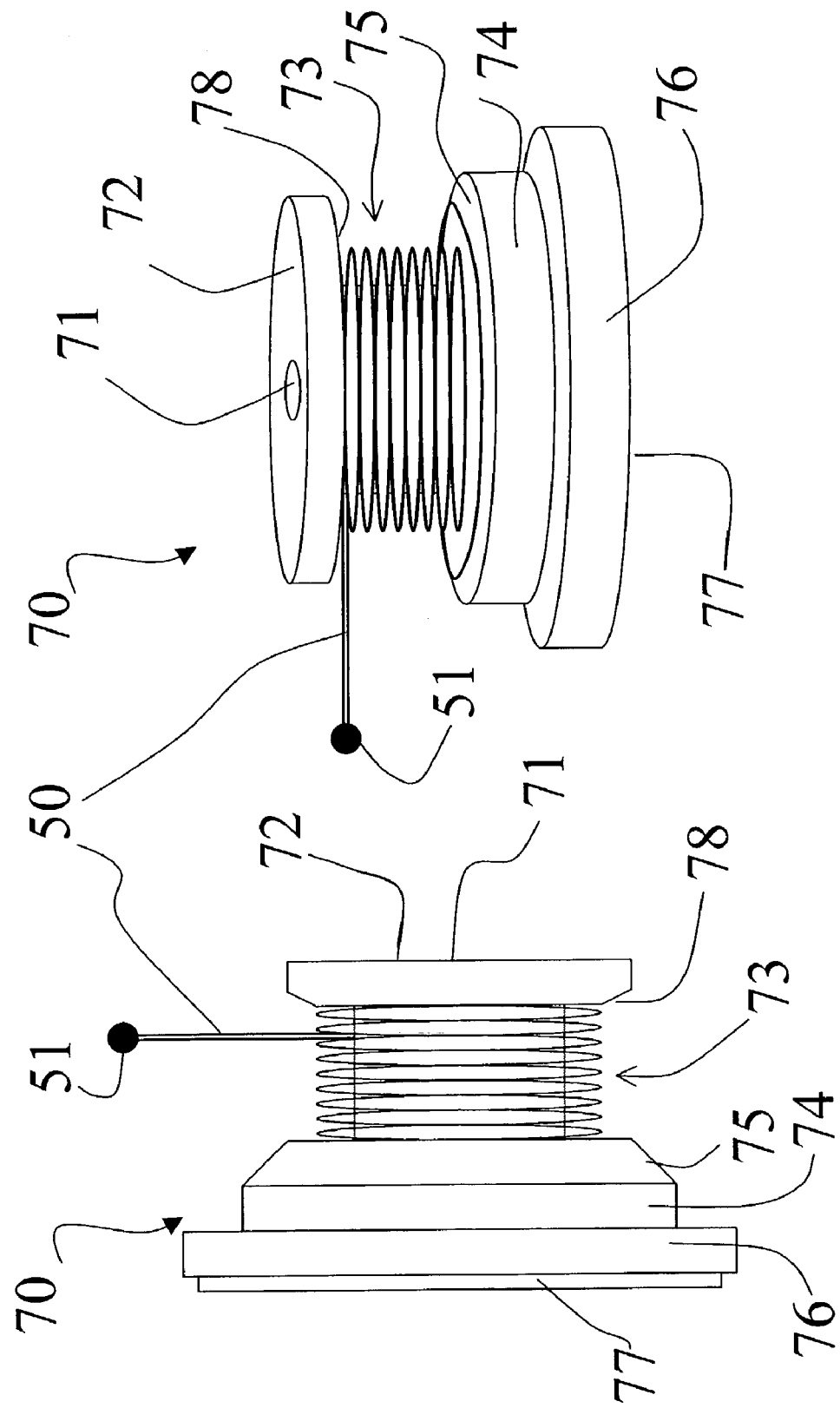
FIG. 19 A is a side view of a suture spool.

As shown in FIGS. 19A and 19B, spool 70 comprises, a spool winding surface 73 interposed between an inner spool face 72 and an outer spool face 74. A bore 71 may be provided for rotation about a spindle in handle 20. Handle 20 is adapted to receive spool 70 for axial rotation therein by any means known in the mechanical arts such as a spindle, bearing race or otherwise. To facilitate proper insertion of spool 70 into handle 20, the diameter of inner spool face 72 may be sized smaller than the diameter of outer spool face 74. Inner and outer faces 72, 74 may also have chamfered surfaces 78, and 75 respectively, facing inwardly to winding surface 73 to facilitate winding of the spools with suture 50. Moreover, the chamfered surface 75 on outer spool face 75 may also provide a bearing/seal interface between it and a corresponding race (not shown) provided in handle 20. A spool end cap 76 may also extend from the outer face 74 to assist in providing a sealing interface. A knob 77 extends from end cap 76 to permit manual rotation of spool 70 for positioning suture leading end 51 proximal fluid jet 33.

In reference to FIGS. 20 and 21, cartridge 55 comprises a suture reservoir 56, a coupler 57, and a protective cap 58. Preferably, coupler 61 is integrally formed with reservoir 63 to limit the presence of small loose articles in the operating room environment, thereby reducing the possibility of inadvertent introduction of foreign matter through an open incision. Reservoir 56 is a hollow member having an open end and a closed end and receives a length of suture 50 therein. A small bore 59 extending through the closed end may be provided to improve entrainment of suture 50. Protective cap 58 is also a hollow member having at least one open end and attaches with coaxial alignments to suture reservoir 56 via coupler 57. In its pre-insertion condition, protective cap 58 receives leading end 51 and a portion of suture 50 therein sufficient to position leading end 51 proximal fluid jet 33 upon insertion of cartridge 55 into the instrument. Protective cap 58 may be detachably coupled to reservoir 56, however, to reduce the presence of loose articles in the operating room environment, protective cap 58 should be captively attached to suture reservoir 56.

As shown in FIGS. 20 B–C and 21 A–B, protective cap 58 is captively and slidably received within suture reservoir 56 such that as cartridge 55 is inserted into handle 20, protective cap 58 retracts within reservoir 56, thereby permitting insertion of leading end 51 proximal fluid jet 33. In this configuration, an interference fit between coupler 57 and protective cap 58 maintains protective cap 58 in position during shipment and storage of cartridge 55, while permitting protective cap 58 to retract during insertion of cartridge 55 into handle 20. To ensure proper delivery and to prevent bunching or binding of suture 50 as protective cap 58 retracts into suture reservoir 56, a portion of protective cap 58 should also extend into suture reservoir 56 and receive a forward portion of the wound or folded suture material 50. In addition to joining protective cap 58 to suture reservoir 56, coupler 57 also provides a coupling interface between cartridge 55 and a suture feed inlet 32 on the instrument handle 20, as shown in FIG. 23.

The coupling interface may be an interference fit, an index slot, or any similar arrangement. The protective cap may also be closed at one end opposite the open end joined to suture reservoir 56. Preferably a pierceable membrane (#) closes this end to enhance the sterility of cartridge 55. In this instance, suture feed inlet 32 may have a sharpened extension for piercing membrane ( ) as cartridge 55 is affixed to instrument 10.

Figure 13:
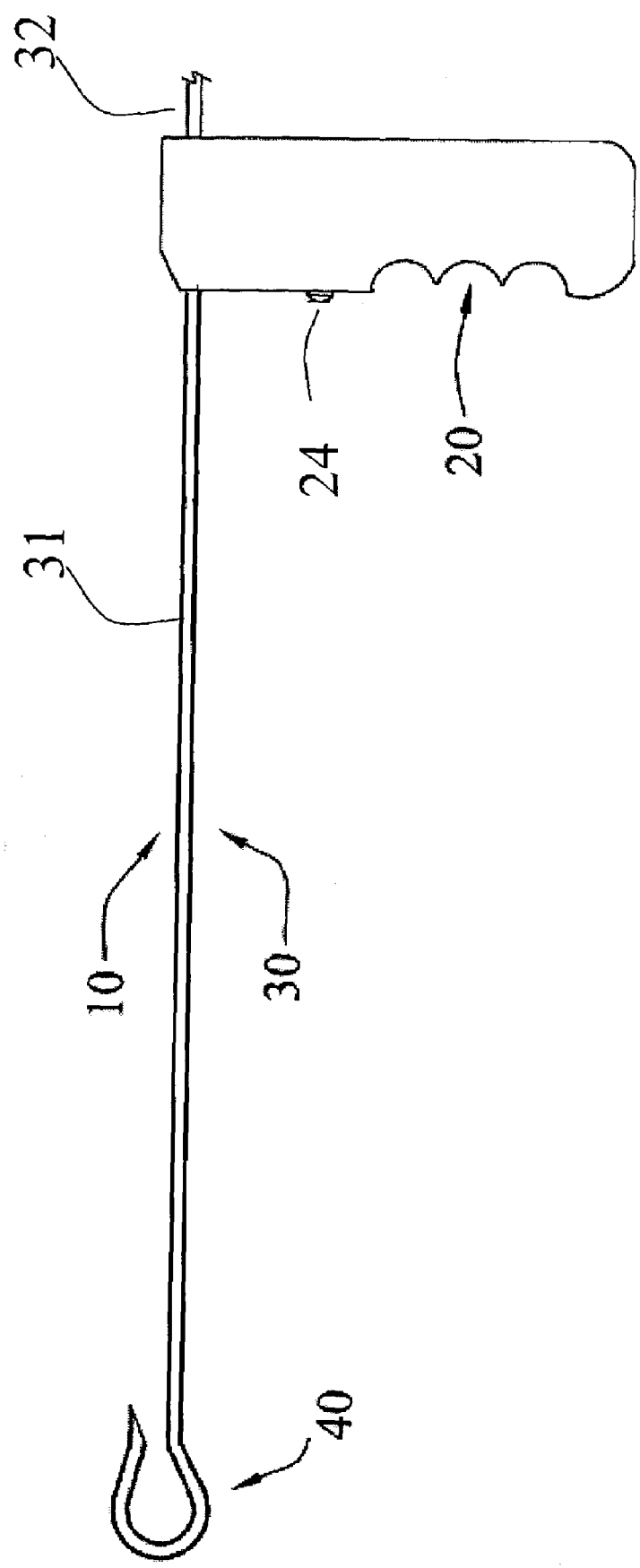
FIG. 13 is a detail view of an open hook tissue penetrating needle.

As discussed previously, a cannula 12 may be employed to retract entry incision 13 and the tissues overlying the site of interest 11. In this case, a simplified embodiment of suture instrument 10 is provided as depicted in FIG. 13. In this simplified suturing instrument 10, hollow tissue penetrating needle 40 is hook shaped to reverse the suture delivery path. Tip 41 is positioned to direct leading end 51 back into the cavity 14 defined by cannula 12 for projection of suture leading end 51 to a point external the patient's body. The surgeon may then grasp leading end 51 and retract the instrument from the body. As the surgeon retracts the suture instrument, additional suture 50 material is drawn through the instrument. As discussed above, if suture 50 is an individual strand, the length of suture 50 should be such that its trailing end 52 will be drawn free of the instrument 10 once the instrument has been withdrawn from cannula 12. The surgeon may then grasp trailing end 52, then tie and manipulate knot 53 to a point adjacent the tissues to be joined 11. If suture 50 is provided in a continuous strand, the surgeon may withdraw a length suture material from the instrument before severing the suture free of the instrument 10.

In the preferred embodiments of suturing instrument 10, the suture return path is provided by the instrument itself. The suture return path is defined by a suture return conduit 36 having a receiving end 37, selectively engageable with tip 41 of hollow tissue penetrating needle 40, and a discharge end 38 proximal handle portion 20. Suture 50, entrained in the pressurized fluid is received by suture return conduit 36 at receiving end 37 and carried thereby to discharge end 38. As suturing instrument 10 is retracted, suture 50 is draw from suture feed conduit 31 and suture return conduit 36 until leading end 51 and trailing end 52 are free of the instrument. The surgeon may then tie and manipulate knot 53 adjacent the site of interest 11.

In the embodiment depicted in FIGS. 1–6, elongated tubular member 30 comprises a selectively extensible sleeve 60, operable by a lever 61, extensibly coupled to handle portion 20 at a sleeve receiver 65. Suture return conduit 36 and suture feed conduit 31 are received internal sleeve 60. Sleeve 60 terminates at a flared portion 62 proximal tissue penetrating needle 40 and receiving end 37 of suture return conduit 36. Actuation of lever 61 extends sleeve 60, such that flared portion 61 urges receiving end 37 and needle 40 into cooperative engagement.

In the embodiment depicted in FIGS. 7 and 8, an actuator lever 63 is pivotally connected to sleeve 60 and selectively urges receiving end 37 into cooperative engagement with a stationary needle 40. An actuator rod 64 or cable operatively connects actuator lever 63 with lever 21 operative from handle portion 20. By selecting a resilient material for suture return conduits, biasing means at leaver 21 may be eliminated. Preferably, actuator rod 64, suture feed conduit 31 and suture return conduit 36 are received within sleeve 60.

Figure 3:
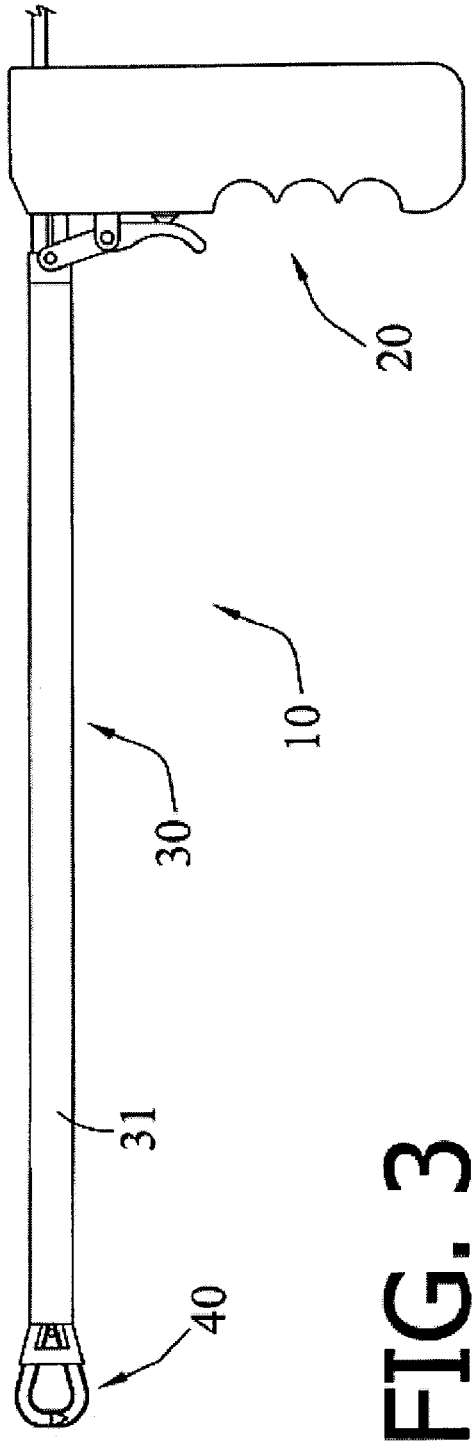
FIG. 3 is a side view of a suture instrument with a tissue penetrating needle in a closed position.
Figure 4:
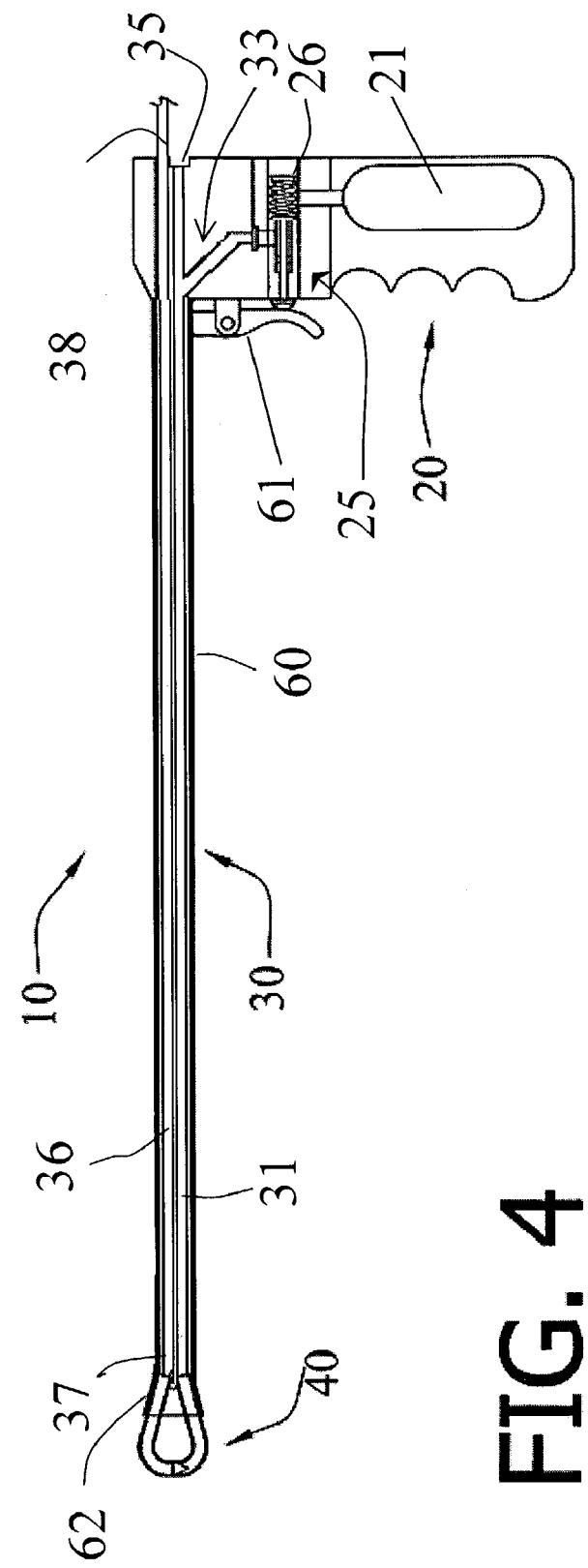
FIG. 4 is a side sectional view of a suture instrument with a tissue penetrating needle in a closed position.
Figure 9:
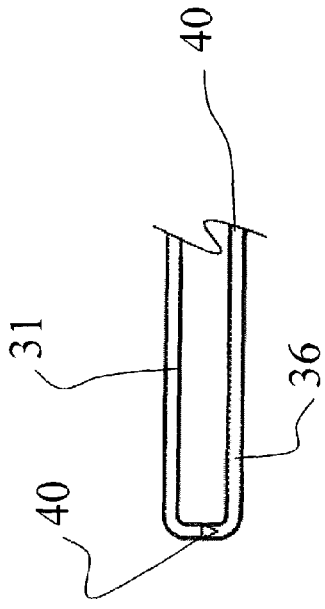
FIG. 9 is a detail view of a scissors actuated tissue penetrating needle closure with the needle in an open position.
Figure 10:
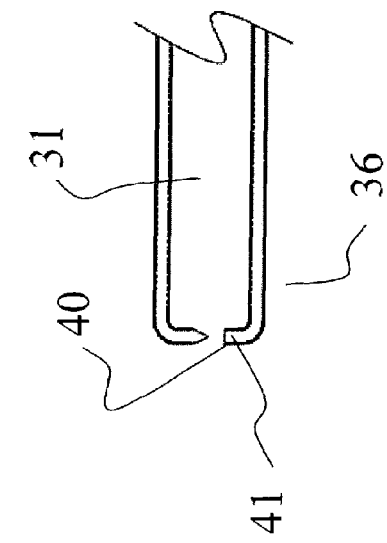
FIG. 10 is a detail view of a scissors actuated tissue penetrating needle closure with the needle in an open position.
Figure 11:
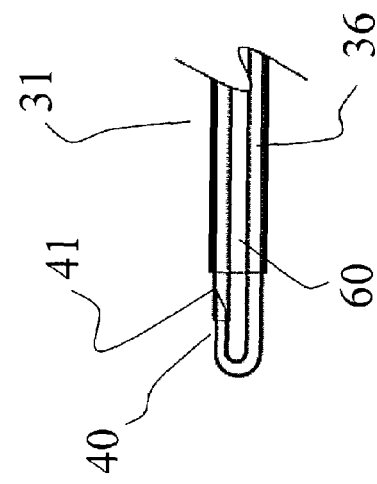
FIG. 11 is a detail view of an extensible suture return conduit tissue penetrating needle closure with the needle in an open position.
Figure 12:
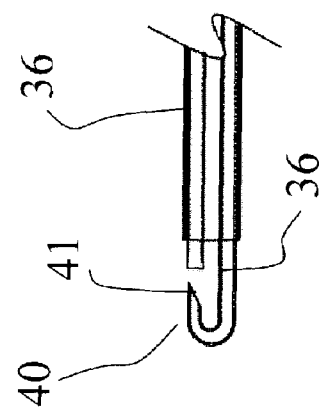
FIG. 12 is a detail view of an extensible suture return conduit tissue penetrating needle closure with the needle in an open position.

In the embodiment depicted in FIGS. 9 and 10, a conventional scissors assembly may be utilized. In the embodiment depicted in FIGS. 11 and 12, hollow tissue penetrating needle 40 is hook shaped, with tip 41 directed towards handle portion 20. Suture return conduit 36 is extensible relative handle 20 for cooperative engagement of receiving end 37 with needle 40. In this instance trigger 27 may be operatively connected to suture return conduit 36, permitting selective positioning of the conduit 36 relative needle 40. Alternatively, a conventional scissors assembly may be employed without detracting from the utility of the invention.

The specific embodiments and features discussed herein and shown in the accompanying drawings are exemplary of a suture instrument according to the present invention. As such many variations or modifications may be made without departing from the scope of the of the appended claims.

What I claim is:

1. In a surgical instrument for joining tissues in a body cavity with a suture, said instrument comprising an elongate tubular member, a handle attached at a proximal end of said elongate tubular member and a hollow tissue penetrating needle attached at a distal end of said elongate tubular member, a suture feed conduit extending between a suture feed inlet proximal said handle and an inner bore of said hollow tissue penetrating needle, said suture feed conduit communicating said suture through said instrument, said hollow tissue penetrating needle, and said body tissues to be joined, wherein the improvement comprises a pressurized fluid suture feed means for entraining said suture in a pressurized fluid stream and carrying said suture through said instrument and said tissues to be joined; and a suture return means for directing said entrained suture to a point external said body cavity.

2. The surgical instrument of claim 1, wherein said pressurized fluid suture feed means comprises a fluid jet, said fluid jet comprising: a pressurized fluid inlet in communication with a selectively releasable pressurized fluid source and a fluid jet outlet in communication with said suture feed conduit, said fluid jet outlet positioned at an angle relative said suture feed conduit such that, upon release of said pressurized fluid source, said pressurized fluid source is delivered through said suture feed conduit and said hollow tissue penetrating needle.

3. The surgical instrument of claim 2, wherein said fluid jet outlet is positioned at an angle relative said suture feed conduit such that, upon release of said pressurized fluid source, a vacuum is induced at said suture feed inlet.

4. The surgical instrument of claim 2, wherein said suture feed inlet is adapted to receive a suture and position a leading end of said suture proximal said fluid jet.

5. The surgical instrument of claim 2, wherein said selectively releasable pressurized fluid source comprises: a pressurized fluid cylinder received in said handle, said pressurized fluid cylinder having an outlet in communication with a valve interposed between said outlet and said fluid jet inlet, and trigger means, operable from said handle, for selectively positioning said valve.

6. The surgical instrument of claim 2, wherein said selectively releasable pressurized fluid source comprises, a valve interposed between said fluid jet inlet and a pressurized fluid conduit which extends through said handle and is adapted to receive a pressurized fluid source external said surgical instrument, and trigger means, operable from said handle, for selectively positioning said valve.

7. The surgical instrument of claim 2, wherein said suture return means comprises a suture return conduit having a first end and a second end, said first end selectively engageable to be in fluid communication with a tip of said hollow tissue penetrating needle, and said second end positioned proximal said handle.

8. The surgical instrument of claim 1, wherein said suture return means comprises a hook defined in said suture feed conduit such that said hollow tissue penetrating needle is directed outwardly of said body cavity such that said entrained suture material may be ejected to a point external the body cavity.

9. The surgical instrument of claim 7, wherein actuator means selectively engage said first end of said suture return conduit and said tip of said hollow tissue penetrating needle.

10. The surgical instrument of claim 9, wherein said actuator means comprises a selectively extensible sleeve enclosing said suture feed conduit and said suture return conduit, said sleeve having a flared portion proximal said hollow tissue penetrating needle and said first end of said suture return conduit, such that upon extension of said sleeve, said hollow tissue penetrating needle and said suture return conduit are urged into communicative engagement.

11. The surgical instrument of claim 9, wherein said actuator means comprises an actuator rod operable on an actuator lever attached to said first end of said suture return conduit to urge said suture return conduit into communicative engagement with said hollow tissue penetrating needle.

12. The surgical instrument of claim 11, further comprising a sleeve enclosing said suture feed conduit and said suture return conduit, wherein said actuator lever is pivotally attached to said sleeve proximal said first end of said suture return conduit.

13. The surgical instrument of claim 9, wherein said actuator means comprises a suture return conduit selectively extensible into communicative engagement with said hollow tissue penetrating needle.

14. The surgical instrument of claim 9, wherein said actuator means comprises a trigger assembly.

15. The surgical instrument of claim 9, wherein said actuator means comprises a scissors assembly.

* * * * *